United States Patent
King-Smith et al.

(10) Patent No.: US 10,067,108 B2
(45) Date of Patent: Sep. 4, 2018

(54) DEVICE FOR DETECTING VOLATILE ORGANIC COMPOUNDS

(71) Applicant: Elemental Sensor LLC, Aptos, CA (US)

(72) Inventors: Oliver P. King-Smith, Aptos, CA (US); Eric K. Hoobler, Santa Cruz, CA (US); Bernardus H. Smit, San Francisco, CA (US)

(73) Assignee: Elemental Sensor LLC, Aptos, CA (US)

( * ) Notice: Subject to any disclaimer, the term of this patent is extended or adjusted under 35 U.S.C. 154(b) by 158 days.

(21) Appl. No.: 15/154,600

(22) Filed: May 13, 2016

(65) Prior Publication Data

US 2016/0334381 A1    Nov. 17, 2016

Related U.S. Application Data

(60) Provisional application No. 62/160,760, filed on May 13, 2015.

(51) Int. Cl.
   *G01N 33/00*   (2006.01)
   *H01J 27/24*   (2006.01)
(52) U.S. Cl.
   CPC .......... *G01N 33/0047* (2013.01); *H01J 27/24* (2013.01)
(58) Field of Classification Search
   CPC .............................. G01N 33/0047; H01J 27/24
   USPC .................................. 250/281, 282, 283, 288
   See application file for complete search history.

(56) References Cited

U.S. PATENT DOCUMENTS

| | | |
|---|---|---|
| 4,034,743 A | 7/1977 | Greenwood et al. |
| 6,493,638 B1 | 12/2002 | McLean et al. |
| 2003/0109794 A1 | 6/2003 | Phillips |
| 2007/0231918 A1 | 10/2007 | Zeng |
| 2009/0090197 A1 | 4/2009 | Finlay et al. |
| 2010/0255198 A1 | 10/2010 | Cleary et al. |
| 2011/0308297 A1 | 12/2011 | Tsuzuki et al. |
| 2013/0253358 A1 | 7/2013 | Phillips |
| 2014/0061459 A1 | 3/2014 | Wilks et al. |
| 2014/0087134 A1 | 3/2014 | Gesford et al. |
| 2014/0288454 A1 | 9/2014 | Paz et al. |
| 2015/0009503 A1 | 1/2015 | Shimoyama et al. |
| 2015/0032019 A1 | 1/2015 | Acker et al. |

(Continued)

OTHER PUBLICATIONS

Altomare et al., Exhaled Volatile Organic Compounds Identify Patients with Colorectal Cancer, British Journal of Surgery 100:144-150 (2013).

(Continued)

*Primary Examiner* — Nicole Ippolito
(74) *Attorney, Agent, or Firm* — Karen Canaan; CanaanLaw, P.C.

(57) ABSTRACT

A device for measuring the concentrations of volatile organic compounds (VOCs) in air. The device includes a sample chamber for accepting a sample of air; at least one ionization source for ionizing VOCs in the sample; an ionic liquid trap containing an ionic liquid that captures the ionized VOCs; a circuit for generating a electric current through the device to run the ionization and capture of the ionized VOCs; and a chemical sensor for detecting and measuring concentrations of the VOCs in the sample of air. The device, which may be hand-held, portable, or designed to sit on a bench top, may be used on any animal, including humans.

51 Claims, 8 Drawing Sheets

(56) References Cited

U.S. PATENT DOCUMENTS

| | | |
|---|---|---|
| 2015/0065901 A1 | 3/2015 | Bhatnagar et al. |
| 2016/0029924 A1 | 2/2016 | Leonhardt et al. |
| 2016/0174875 A1 | 6/2016 | Forster et al. |
| 2016/0193543 A1 | 7/2016 | Kim et al. |
| 2017/0035326 A1* | 2/2017 | King-Smith ............ A61B 5/097 |

OTHER PUBLICATIONS

Ametepe et al., Characterization and Modeling of a Microwave Driven Xenon Excimer Lamp, Journal of Applied Physics 85(11):7505-7510 (1999).

Boichenko et al., Emission Efficiency of Exciplex and Excimer Molecules Pumped by a Barrier Discharge, Laser Physics 10(2):540-552 (2000).

Biochenko et al., Exciplex Rare-Halide Lasers, Laser Physics 10(6):1159-1187 (2000).

Braithwaite, Introduction to Gas Discharges, Plasma Sources Science and Technology 9:517-527 (2000).

Chistyakov et al., An Excimer-based FAIMS Detector for Detection of Ultra-low Concentration of Explosives, Proceedings of SPIE 9072:(907211)1-8 (2014).

Eliasson et al., Modelling of Dielectric Barrier Discharge Chemistry, Pure and Applied Chemistry 66(6):1275-1286 (1994).

Gellert and Kogelschatz, Generation of Excimer Emission in Dielectric Barrier Discharges, Applied Physics B 52:14-21 (1991).

Gonzales-Miquel et al., Selection of Ionic Liquids for Enhancing the Gas Solubility of Volatile Organic Compounds, The Journal of Physical Chemistry B 117:296-306 (2013).

Hanley et al., Light and Molecular Ions: The Emergence of Vacuum UV Single-Photon Ionization in MS, Analytical Chemistry 81(11):4174-4182 (2009).

Heintz et al., Activity Coefficients at Infinite Dilution and Enthalpies of Solution of Methanol, 1-butanol, and 1-hexanol in 1-hexyl-3-methyl-imidazolium bis(trifluoromethyl-sulfonyl) imide, Journal of Chemical Thermodynamics 39:268-274 (2007).

Huffman et al., Rare Gas Continuum Light Sources for Photoelectric Scanning in the Vacuum Ultraviolet, Applied Optics 4(12):1581-1588 (1965).

Kogelschatz, Dielectric-Barrier Discharges: Their History, Discharge Physics, and Industrial Applications, Plasma Chemistry and Plasma Processing 23(1):1-46 (2003).

Kogelschatz, Dielectric-Barrier Discharges: Principle and Applications, Journal de Physique IV (France) 7:(C4) 47-66 (1997).

Kogelschatz et al., High-intensity Sources of Incoherent UV and VUV Excimer Radiation for Low-Temperature Materials Processing, Applied Surface Science 168:29-36 (2000).

Kozlova et al., Activity Coefficients at Infinite Dilution of Hydrocarbons, Alkylbenzenes, and Alcohols in the Paramagnetic Ionic Liquid 1-butyl-3-methyl-imidazolium tetrachloridoferrate(III) using Gas-Liquid Chromatography, Journal of Chemical Thermodynamics 41:330-333 (2009).

Kulajanpeng et al., Ionic-Liquid Based Separation of Azeotropic Mixtures, Chemical Engineering Transactions 39:517-522 (2014).

Lomaev et al., Excilamps and Their Applications, Process in Quantum Electronics 36:51-97 (2012).

Lomaev et al., Excilamps: Efficient Sources of Spontaneous UV and VUV Radiation, Physics-Uspekhi (Advances in Physical Sciences) 46(2):193-209 (2003).

Lomaev et al., On the Formation of a Barrier Discharge in Excilamps, Technical Physics 52(8):1046-1052 (2007).

McCulloch et al., Diagnostic Accuracy of Canine Scent Detection in Early- and Late-Stage Lung and Breast Cancers, Integrative Cancer Therapies 5(1):30-39 (2006).

Morgan et al., Diffusivities of Gases in Room-Temperature Ionic Liquids: Data and Correlations Obtained Using a Lag-Time Technique, Industrial and Engineering Chemistry Research 44(13):4815-4823 (2005).

Muhlberger et al., Single Photon Ionizatoin Time-of-Flight Mass Spectrometry with a Pulsed Electron Beam Pumped Excimer VUV Lamp for On-Line Gas Analysis: Setup and First Results on Cigarette Smoke and Human Breath, Analytical Chemistry 77(22):7408-7414 (2005).

Paniker, Ionization of Air by Corona Discharge, Masters Thesis (in Aerospace Engineering) of Philip Koshy Panicker, University of Texas at Arlington, Aug. 2003.

Sanchez et al., Blood Cells as a Source of Transcriptional Biomarkers of Childhood Obesity and Its Related Metabolic Alterations: Results of the IDEFICS Study, Journal of Clinical Endocrinology and Metabolism 97(4):E648-E652 (2012).

Schitz et al., Modular Excilamps of Barrier Discharge, Beam and Plasma Sources Conference, Institute for High-Current Electronics, Tomsk, Russia, Poster Session, pp. 48-50 (1998).

Scott, Donald E., Primer on "Gas Discharges" (Plasmas) (2013), published at http://electric-cosmos.org/PrimerAboutGD.pdf (website of Donald E. Scott).

Tabrizchi et al., Design and Optimization of a Corona Discharge Ionization Source for Ion Mobility Spectrometry, Review of Scientific Instruments 71(6):2321-2328 (2000).

Tarasenko et al., Excilamps as Efficient UV-VUV Light Sources, Pure and Applied Chemistry 74(3):465-469 (2002).

Wilkinson and Tanaka, New Xenon-Light Source for the Vacuum Ultraviolet, Journal of the Optical Society of America 45(5):344-349 (1955).

Wilkinson and Byram, Rare Gas Light Sources for the Vacuum Ultraviolet, Applied Optics 4(5):581-588 (1965).

Yan et al., 121.6 nm Radiation Source for Advanced Lithography, Journal of Vacuum Science & Technology B 20 (6):2574-2577 (2002).

Non-Final Office Action dated Jun. 29, 2018, for U.S. Appl. No. 15/232,547.

* cited by examiner

DEVICE FOR DETECTING VOLATILE ORGANIC COMPOUNDS

CROSS-REFERENCE TO RELATED APPLICATIONS

This application claims priority under 35 U.S.C. 119(e) to U.S. Provisional Application No. 62/160,760, filed on May 13, 2015, which is incorporated in its entirety herein.

TECHNICAL FIELD

The present invention relates generally to devices for detecting volatile organic compounds (VOCs). More specifically, the present invention relates to a gas sensing device for detecting VOCs in a sample of air, such as for example, the breath of a human or animal.

BACKGROUND OF THE INVENTION

Medical researchers have known for many years that diseases can be detected by biomarkers in the breath. See, e.g., Buszewski et al., *Bioanalysis* 5(18):2287-2306 (2013). In one application of this knowledge, researchers have trained dogs to smell for cancer. See, e.g., McCulloch et al., *Integrative Cancer Therapies* 5(1):30-39 (2006). The range of diseases that have been detected by smell are lung cancer, Parkinson's, prostate cancer, breast cancer, colon cancer, small intestine bacterial overgrowth, and asthma.

When patients breathe in and out, they release volatile organic molecules that are biomarkers for particular diseases. Changes in the concentration of the biomarkers can be used to identify the disease. These biomarkers are often in very low concentrations, ranging from a few parts per million to under one part per billion.

VOCs make up the majority of the scents and smells human and animals can sense. While smell has not been formally used in routine medical practice in recent times, there are well known scents associated with particular conditions. For example, the smell of death is created by VOCs, in particular putrescine and cadaverine, which are released when cells die. Other VOCs, such as ketones, are exhaled if there is not enough insulin to help the body use sugar for energy. Lung cancer has over 40 known VOCs that researches have shown can indicate lung cancer.

A major challenge in measuring the VOCs in breath is the complexity of the sample. There are over 1,000 known compounds in breath. Trying to separate and measure all these compounds has been a logistical challenge for makers of devices. Simple devices often can only measure a class of compounds, or have unknown specificity and selectivity towards different VOCs.

Devices used in research have suffered from being very complex to use, making them difficult to deploy in a standard clinical environment, or they have been to very expensive to use making them unattractive for a screening test. It is therefore appreciated there is a need in the art for a small and inexpensive device that can be used to measure biomarkers in the breath.

SUMMARY OF THE INVENTION

The present invention overcomes the need in the art by providing a device for measuring concentrations of VOCs in air, such as for example, the breath of an animal. The present invention can detect multiple VOCs at different concentrations.

In one embodiment of the invention, there is provided a device comprising: (a) a sample chamber for accepting a sample of air; (b) at least one ionization source for ionizing volatile organic compounds (VOCs); (c) an ionic liquid trap comprising an ionic liquid; and (d) a bias circuit for generating an electric field, wherein the bias circuit is connected to the ionic liquid trap and a conductive element of the device, wherein ionization of VOCs in the sample of air by the ionization source and generation of the electric field by the bias circuit drives ionized VOCs from the sample chamber into the ionic liquid trap. The device may further comprise a chemical sensor.

In another embodiment of the invention, there is provided a device comprising: (a) a sample chamber for accepting a sample of air; (b) at least one ionization source for ionizing volatile organic compounds (VOCs) present in the sample of air; (c) an ionic liquid trap comprising an ionic liquid that captures ionized VOCs from the sample chamber, wherein the ionized VOCs are deionized in the ionic liquid trap and reionized upon release from the ionic liquid trap; and (d) a chemical sensor in communication with the ionic liquid trap, wherein the chemical sensor identifies ionized VOCs released from the ionic liquid trap. The device may further comprise a bias circuit.

In a further embodiment of the invention, there is provided a device comprising: (a) a sample chamber for accepting a sample of air; (b) at least one ionization source for ionizing volatile organic compounds (VOCs); (c) an ionic liquid trap comprising an ionic liquid; and (d) a bias circuit for generating an electric field, wherein the bias circuit is connected to the ionic liquid trap and a conductive element of the device; and (e) a chemical sensor for identifying and measuring concentrations of VOCs, wherein ionization of VOCs in the sample of air by the ionization source and generation of the electric field by the bias circuit drives ionized VOCs from the sample chamber into the ionic liquid trap.

The sample of air, which may be obtained from any animal, including a human, may be in the range of about 10 mL to about 5000 L.

In one embodiment, the sample chamber of the device may comprise an input port for accepting the sample of air. A moisture filter may be used to reduce moisture content of the sample of air entering into the sample chamber. The sample chamber may further comprise an output port. The input port and the output port may be separate ports or a single port. The sample chamber of the device may be cleaned by flushing a neutral gas, such as clean air, through the input port and/or the output port.

In another embodiment, the sample chamber may comprise a floor, a ceiling, and an optional heating element. The heating element may run between about 30° C. to about 500° C. The heating of the sample chamber may prevent VOCs from condensing out of the air sample. In a further embodiment, the heating element may be used to clean the sample chamber.

In one embodiment, the at least one ionization source is selected from the group consisting of electromagnetic radiation, ultraviolet (UV) light, radioactive material, corona discharge, chemical ionization, electron impact ionization, high speed particles, x-ray ionization, electrospray, ion source, and combinations thereof. The at least one ionization source may comprise at least two different ionization sources to drive VOCs of differing ionization energies from the sample chamber to the different ionic liquid traps. The UV light may be selected from the group consisting of direct current (DC) type UV bulbs with internal electrodes, lasers, excimer lamps, plasma, arc lamps, and light emitting diodes (LEDs). In another embodiment, the electromagnetic radiation may be in the range of about 1 µeV to about 16 eV. In a further embodiment, the UV light may be in the range of about 3 eV to 16 eV.

In another embodiment, the ionization source may be separate from the sample chamber. In a further embodiment, the ionization source may be embedded in the sample chamber.

In one embodiment, VOCs in the ionic liquid trap may be released back into the sample chamber by excitation of the VOCs in the ionic liquid trap. The VOCs in the ionic liquid may be excited by an energy source selected from the group consisting of heat, acoustic waves, ultrasound, microwaves, infrared radiation, pressure changes in the atmosphere above the iconic liquid trap, and combinations thereof.

In another embodiment, an electrical insulator may separate the ionic liquids in the ionic liquid trap from the sample chamber.

In a further embodiment, the ionic liquid trap comprises an array of sensors containing the ionic liquid, wherein each sensor in the array may contain the same ionic liquid or a different ionic liquid. In one embodiment, the sensors are selected from the group consisting of ion sensitive field effect transistors (ISFET), dielectric spectroscopy, impedance, and viscosity changes, and combinations thereof. In another embodiment, the sensors may have individual heating and/or cooling elements.

In one embodiment, the chemical sensor may identify VOCs in the ionic liquid trap, wherein the chemical sensor is in communication with the ionic liquid trap. The chemical sensor may further measure concentrations of the VOCs in the ionic liquid trap. Alternatively, the chemical sensor may identify VOCs released from the ionic liquid trap to the sample chamber. The chemical sensor may further measure concentrations of the VOCs released from the ionic liquid trap to the sample chamber.

In another embodiment, the chemical sensor comprises an outlet port, an electrical waveform, and an ion sensor, wherein the ionized VOCs released from the ionic liquid trap pass through the outlet port and the electrical waveform directs the ionized VOCs to the ion sensor for identification.

In a further embodiment, the chemical sensor comprises an inlet port and an ion sensor, wherein introduction of a neutral gas, such as for example clean air, in a steady stream into the inlet port causes different ionized VOCs in the sample chamber to reach the ion sensor at different times.

In one embodiment, the ionic liquid trap further comprises a circuit and the chemical sensor comprises a measuring device selected from the group consisting of impedance meters, vector network analyzers, time-domain reflectometers, and combinations of thereof. Upon application of an electric current from the measuring device to the circuit, altered electrical properties in the circuit are measured by the measuring device, wherein the electrical properties of the circuit are altered by VOCs in the ionic liquid trap.

In another embodiment, the bias circuit may include a counter electrode, wherein an electric field is generated between the ionic liquid and the counter electrode. In a further embodiment, the counter electrode may be located in the sample chamber.

The devices as described herein may be hand-held devices, portable devices, or bench-top devices.

Additional aspects and embodiments of the invention will be provided, without limitation, in the detailed description of the invention that is set forth below.

DETAILED DESCRIPTION OF THE INVENTION

Figure 1:
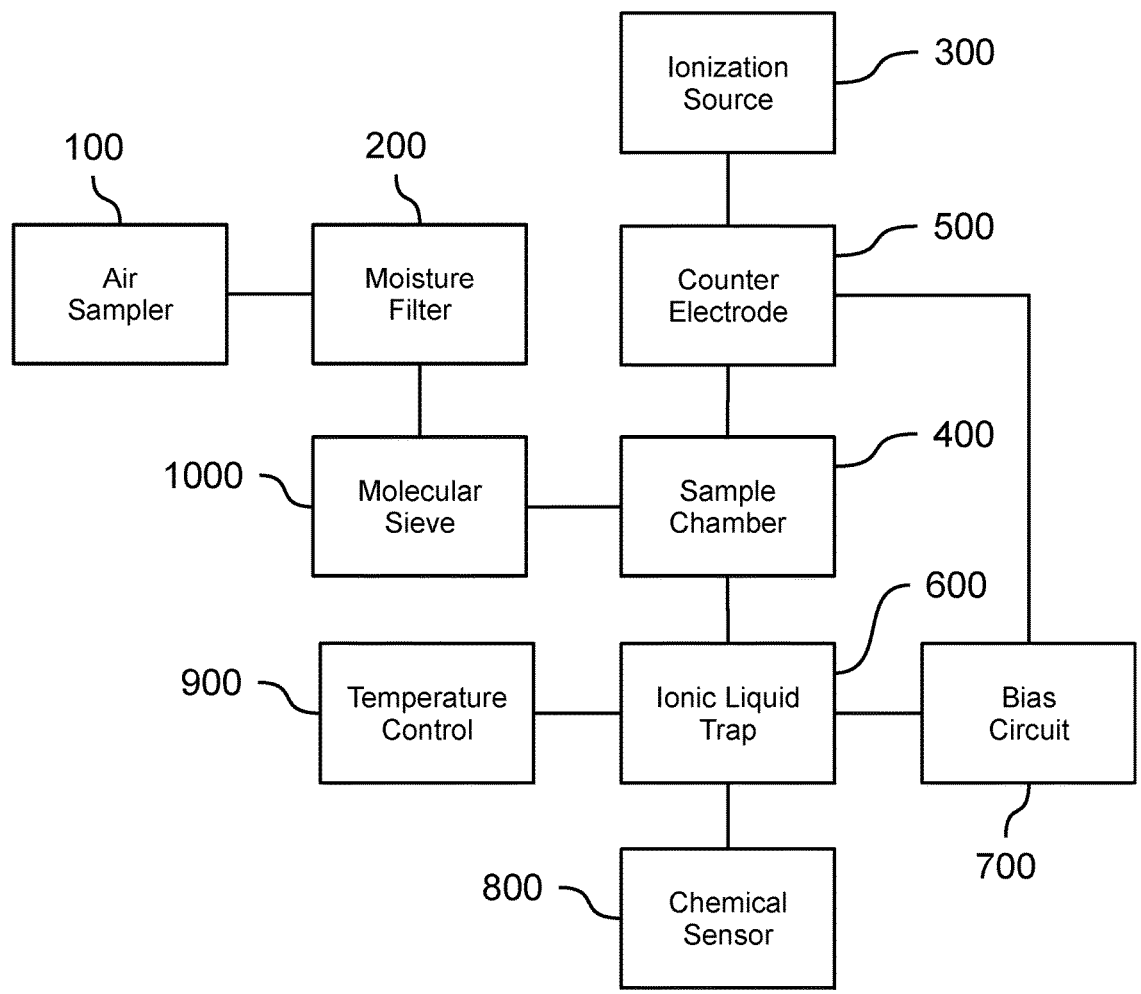
FIG. 1 is a schematic diagram showing a representative embodiment of the gas sensing device of the present invention.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "about" is used in its usual sense to convey a measurement that one of ordinary skill in the art would reasonably convey to be close to a stated numerical figure.

As used herein, the term "animals" is meant to refer to any animal species, including all vertebrate and invertebrate animals, including without limitation, mammals (including humans), reptiles, amphibians, and birds. While the gas sensing device of the present invention has its greatest widespread application with humans, the device is not meant to be limited to application to any one species of animal.

As used herein, the term "neutral gas" is meant to refer to an inert, stable gas that does not react under normal conditions. Examples of neutral gases that may be used with the gas sensing device of the present invention include without limitation, clean air, helium, and nitrogen. As will be appreciated by those of skill in the art, other non-reactive neutral gases may have applicability with the gas sensing devices described herein.

In all embodiments of the gas sensing device, the at least one ionization source 300 may be any suitable source known to those of skill in the art to ionize VOCs. Examples of such ionization sources include without limitation, electromagnetic radiation, ultraviolet (UV) light, radioactive material, corona discharge, chemical ionization, electron impact ionization, high speed particles, x-ray ionization, electrospray, ion source, and combinations thereof. Where the ionization source is electromagnetic radiation, the electromagnetic radiation will be applied in the range of about 1 µeV to about 16 eV. Where the ionization source is UV light, the UV light may be any UV light source, including without limitation, direct current (DC) type UV bulbs with internal electrodes, lasers, excimer lamps, plasma, arc lamps, and light emitting diodes (LEDs). In one embodiment, the UV light is applied in the range of about 3 eV to about 12 eV. In another embodiment, the UV light is in the range of about 8 eV to about 12 eV. It will be appreciated by one of skill in the art that UV light in the 8-12 eV range will ionize almost all VOCs while not ionizing other components in breath, such as nitrogen, oxygen, carbon monoxide, carbon dioxide, or water vapor. Where the ionization source is electron impact ionization, an electron gun may be used to deliver the ionizing energy. In one embodiment, the electron impact ionization is applied in the range of about 1 eV to about 100 eV.

In all embodiments of the gas sensing device, a moisture filter 200 may be used in conjunction with a sample chamber 400 to reduce moisture content of an air sample entering into the sample chamber.

In embodiments of the gas sensing device that include a sample chamber 400 having an input port 402 and an output port 403 and/or a chemical sensor 800 having either an outlet port 806 or an inlet port 807, it may be necessary or desirable to clean the sample chamber 400 or the chemical sensor 800. The sample chamber 400 may be cleaned by flushing a neutral gas through the input and output ports in either direction. The chemical sensor 800 may be similarly cleaned by flushing a similar neutral gas into the outlet 806 or inlet 807 ports.

In all embodiments of the gas sensing device, ionic liquids in an ionic liquid trap 600 are used to capture VOCs from an air sample. As is known to those of skill in the art, ionic liquids can be designed to absorb VOCs. Ionic liquids that may be used with gas sensing devices of the present invention include any tunable liquid that can absorb VOCs. In one embodiment, the ionic liquids may be designed to absorb polar versus non-polar VOCs. In another embodiment, the ionic liquids may be selected from the group consisting of ammonium-based ionic liquids, imidazolium-based ionic liquids, piperidinium-based ionic liquids, pyridinium-based ionic liquids, pyrrolidinium-based ionic liquids, phosphonium-based ionic liquids, and sulfonium-based ionic liquids. One example of an ionic liquid that may be used with the present invention is 1-butyl-3-methylimidazolium bis(trifluoromethanesulfonyl)imide (Sigma-Aldrich, St. Louis, Mo., USA). It is important to note that within the context of the present invention, the ionic liquids must be tuned such that any VOCs absorbed into the ionic liquid can be released from the ionic liquid trap 600.

In all embodiments of the gas sensing device that include the release of VOCs from the ionic liquid trap, the release of the VOCs is accomplished by applying an energy source to the ionic liquid trap that excites the VOCs. Examples of such energy sources include without limitation, heat, acoustic waves, ultrasound, microwaves, infrared radiation, pressure changes in the atmosphere above the iconic liquid trap, and combinations thereof.

It is to be understood that all embodiments of the gas sensing device may be a small hand-held or portable device. Alternatively, the gas sensing device may also be designed to be a bench top device.

Referring to the figures, FIG. 1 shows a block diagram schematic of the gas sensing device of the present invention. The gas sensing device collects an air sample with the air sampling device 100 (also referred to herein as the "air sampler"), which has a shut off value to allow a specific quantity of air to enter and be held inside the gas sensing device. In one embodiment, the air sampling device 100 is connected to an optional moisture filter 200. If there is no need for a moisture filter, the air sampling device is connected directly to the sample chamber 400.

The air sampler 100 is designed to detect and capture a representative sample of air. For example, the air sampler 100 can capture a sample of air after a human subject has breathed clean dry air. The length of time it takes to analyze a sample of air is typically less than 10 minutes. In one embodiment, the gas sensing device may be used for lung cancer detection. For this application, the air sampler 100 will admit air from the lungs, not the headspace, into the sample chamber 400, either directly from the air sampler 100 or alternatively through the moisture filter 200. The air sampler 100 is capable of admitting the lung air (as opposed to any non-pulmonary air present in the air sampler) by monitoring moisture and $CO_2$ levels in the air sample.

With continued reference to FIG. 1, the sample chamber 400 is typically designed to hold a representative air sample, such as for example, a sample of air from a person's breath. In some embodiments, the sample chamber 400 is pressurized; the pressure can be induced by injecting a known volume of air sample into the sample chamber 400. The sample chamber 400 can be made of any material that will not absorb or interact with VOCs. Examples of such materials include without limitation, aluminum or stainless steel, glass, plastics, and PTFE (polytetrafluoroethylene, sold commercially as TEFLON®, E.I. Dupont DeNemours & Co., Wilmington, Del., USA). Within the context of the present invention, it is advantageous if the material for the sample chamber 400 can be heated above 150° C. to volatize any VOCs that may have stuck to the walls of the chamber.

Once an air sample is in the sample chamber 400, an ionization source 300 is used to ionize the gas components in the air sample. The ionization source may be selected from any of the ionization sources described herein, such as for example, electromagnetic radiation, ultraviolet (UV) light, radioactive material, corona discharge, chemical ionization, electron impact ionization, high speed particles, x-ray ionization, electrospray, ion source, and combinations thereof.

An electric field is induced in the sample chamber 400 by the bias circuit 700. The bias circuit 700 may have more than one electrode. In one embodiment, the bias circuit 700 develops an electric field from the counter electrode 500 to the ionic liquid trap 600. In another embodiment, one electrode for the bias circuit 700 is located in the ionic liquid trap 600 while the other electrode for the bias circuit 700 is connected to the counter electrode 500. In some embodiments, the counter electrode 500 may be combined with the sample chamber 400. In other embodiments, the counter electrode 500 is a separate element.

While the bias circuit 700 is on, ionized VOCs in the sample chamber 400 are driven into the ionic liquid trap 600. The moisture filter 200 may be used to reduce the moisture content of the sample when ionic liquids in the ionic liquid trap 600 might have an adverse reaction to water vapor. The bias circuit 700 can be operated with a fixed potential or with a variable potential. When used in a variable potential, it can be used to drive preferred VOCs into the ionic liquid trap 600. In one embodiment, the ionic liquid trap 600 can contain ionic liquids that are selective for particular VOCs of interest. In another embodiment, the ionic liquids can be selected to less readily adsorb water and VOCs that are not of interest. In a further embodiment, the VOCs are released from the ionic liquid trap using any energy source that excites the VOCs, as previously described and defined herein. As will be appreciated by those of skill in the art, the ionic liquid should be capable of withstanding exposure to UV light (i.e., the ionic liquid should not be capable of breaking down under exposure to UV light).

After the bias circuit 700 is turned off, the chemical sensor 800 can detect VOCs in the ionic liquid trap 600, or detect VOCs after they have been released from the ionic liquid trap 600.

The ionic liquid trap 600 contains, is combined with, or is connected to, a chemical sensor system 800. Examples of chemical sensors that may be integrated into the gas sensing device of the present invention include without limitation, liquid chromatography systems, ion mobility spectrometers, silicon sensors or semiconductor arrays, impedance analyzers, distillation systems, gas chromatographs, capacitive sensors, infrared sensors, Raman spectrometers, surface enhance Raman spectrometers, acoustic spectrometers, photo ionization detectors, flame ionization detectors, or any other sensor known to those skilled in the art. In one embodiment, the ionic liquid trap 600 and the chemical sensor 800 are combined using technologies known to those skilled in the art, such as for example, an ion sensitive field effect transistors, dielectric spectroscopy, and impedance analysis. In addition, the chemical sensor 800 can be integrated with the ionic liquid trap 600 using impedance measurements, and more generally dielectric spectroscopy where the impedance is measured over frequency. The chemical sensor can then measure the changes in the dielectric constants over the frequency of the ionic liquids in the ionic liquid trap, as the VOCs are driven out of the ionic liquid trap. As previously noted, VOCs may be driven out of an ionic liquid trap by applying an energy source to the ionic liquid trap, wherein the energy source may be selected from the group consisting of heat, microwaves, ultrasound, infrared radiation, acoustic waves, pressure changes in the atmosphere above the iconic liquid trap, and combinations thereof.

The ionic liquid trap 600 optionally has a temperature sensor and a temperature control unit 900 connected to it. The temperature control unit 900 can be used to cool or heat the ionic liquid trap 600 to help capture ionized VOCs from the air sample in the sample chamber 400. To aid with detection, the temperature control unit 900 can heat the ionic liquid trap 600 to change properties of the VOCs in the ionic liquid trap 600. Examples of properties of VOCs that may be changed upon heating include without limitation, viscosity and electrical conductance or impedance. It is possible to measure or control the temperature of the ionic liquid trap 600 with the temperature control unit 900.

As noted above, the ionic liquid trap 600 is structured in a way that it may contain a plurality of ionic liquid types. An advantage of ionic liquids is that many have negligible vapor pressure. Because of their negligible vapor pressure, they will not contaminate any external chemical sensor 800, as the VOCs are driven out of the ionic liquid by the temperature control unit 900.

In one embodiment of the present invention, the ionic liquid trap 600 can be moved manually or automatically from the sample chamber 400 to the chemical sensor 800. In another embodiment, the ionic liquid trap 600 can be removed from the sample chamber 400 to be analyzed in a separate chemical sensor 800, which need not be integrated into the gas sensing device. For example, the chemical sensor may be situated in a different location from the gas sensing device.

In another embodiment of the present invention, the ionic liquid trap 600 may need to be replaced between air samples. In this regard, the ionic liquid trap 600 should be designed such that it can be user replaceable.

In other embodiments, the chemical sensor 800, the ionic liquid, and/or the ionic liquid trap 600 may need to be replaced between air samples. To facilitate this, the chemical sensor 800 may be designed to be external to the ionic liquid trap 600. When the chemical sensor is external to the ionic liquid trap, it may be necessary to clear the air in the sample chamber 400 with a neutral gas. In one embodiment, the neutral gas used to flush the sample chamber is clean air. When the air sample has been purged from the sample chamber 400, the VOCs in the ionic liquid trap may then be released, by heating the ionic liquid trap with the temperature control unit 900, back into the sample chamber for analysis by the chemical sensor 800. Then the VOCs trapped in the ionic liquid trap 600 can be driven back into the sample chamber 400 by heating the ionic liquid trap 600 with the temperature control unit 900. Once the VOCs in the ionic liquid trap 600 are released back into the sample chamber, the chemical sensor 800 can identify and measure the concentration of VOCs in the air sample.

An advantage of the present invention includes, without limitation, a way of concentrating and detecting ionized VOCs in an air sample. It will be appreciated by those skilled in the art, that the ionization source 300 combined with the bias circuit 700 can temporarily increase the concentration of VOCs in the ionic liquid trap 600 by several orders of magnitude. This extends the low end detection range of a chemical sensor 800 integrated into the ionic liquid trap by the amount of the concentration.

Another advantage of the present invention is that VOCs driven into the small head space above the ionic liquid trap 600 will extend the sensitivity of any attached chemical sensor 800. It will be further noted, that if the temperature control unit 900 is used to drive VOCs from the ionic liquid trap, a separation in the VOCs will occur based on their different boiling points.

A further advantage of the present invention is that if the ionization source 300 is a UV light source, only VOCs in the air sample will become ionized. With reference to FIG. 1, these VOCs will be driven by the bias circuit 700 into the ionic liquid trap 600.

Figure 2:
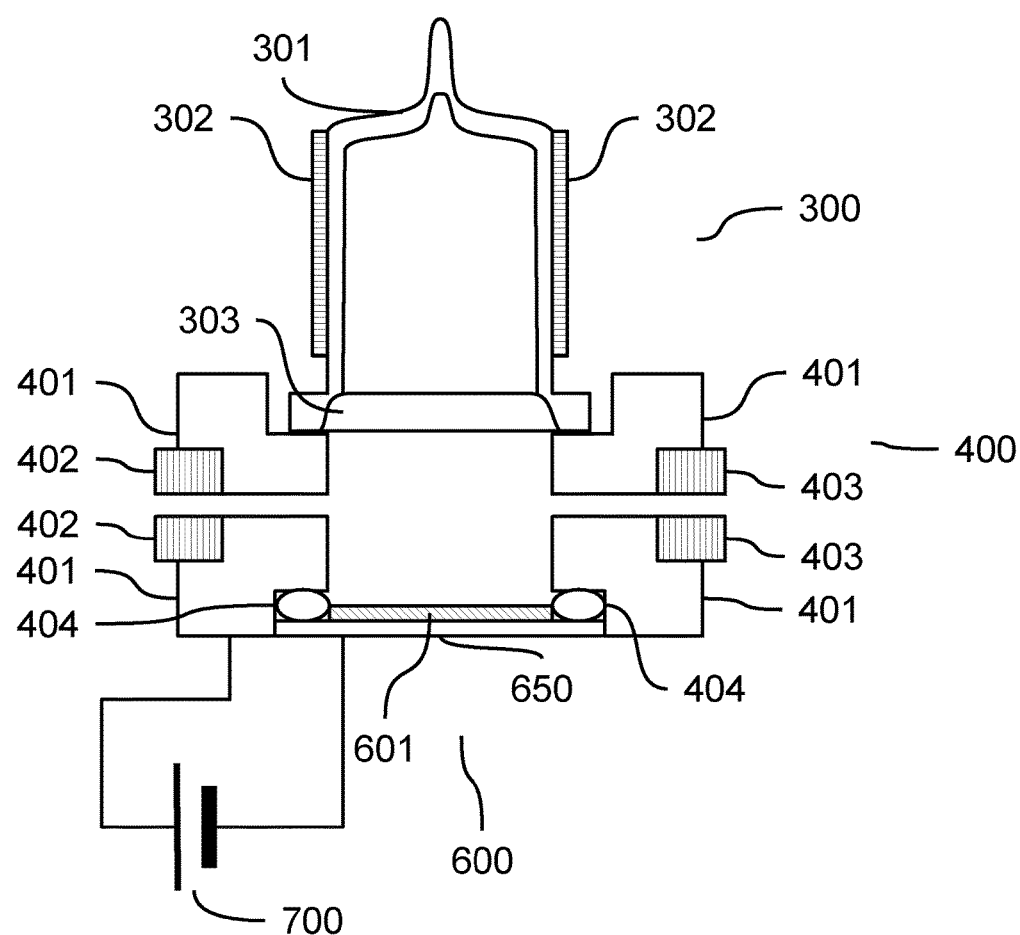
FIG. 2 is a partial longitudinal sectional view of one embodiment of the present invention, which depicts a gas sensing device with an ionization source (300) and its parts, a sample chamber (400) and its parts, an ionic liquid trap (600) and its parts, and a bias circuit (700).

Referring now to FIG. 2, here is a partial cross section of one embodiment of the present invention. In one embodiment, the ionization source 300 may be selected from any of the ionization sources described and defined herein. In another embodiment, the ionization source 300 is UV light.

In a further embodiment, which is depicted in FIG. 2, the ionization source is a UV bulb 301. It is to be understood that the depiction of the UV bulb 301 in FIG. 2 is meant to be illustrative of one embodiment of the invention and in this regard is not meant to be limiting. The UV bulb is energized by electrodes 302 and the UV light is admitted into the sample chamber 400 by the UV window 303. As shown, the sample chamber 400 comprises sample chamber walls 401, which have a gas input port 402 and a gas output port 403. As shown, the bias circuit 700 uses the sample chamber walls 401 as the counter electrode. An optional electrical insulator 404 can be provided to separate the ionic liquid 601 from the chamber walls 401. At the bottom of the sample chamber is the ionic liquid trap 600 in this embodiment composed of an ionic liquid 601 and a circuit board 650. The bias circuit 700 is connected to the circuit board 650.

In more detail, still referring to FIG. 2, an air sample enters the sample chamber 400 through the gas input port 402. Once an air sample is in the sample chamber, the UV bulb 301 can be activated to ionize VOCs with ionization energies, below that of the UV light, emitted by the UV window 303. When the bias circuit 700 is activated with a positive potential on the chamber walls 401 and negative potential on the circuit board 650, electrons will be pulled towards the chamber walls, and positively charged VOCs will be pulled towards the ionic liquid trap 600.

In more detail, still referring to FIG. 2, the ionization source 300, is selected to be preferential for ionizing VOCs by the light emitted from the UV window 303. Referring to the UV bulb 301 shown therein, the size of a typical UV bulb is 5-20 mm in diameter and 20-50 mm in height. The spacing between the UV window and the ionic liquid 601 can be optimized for different applications as is well known to those skilled in the art of photoionization, but is typically less than 20 mm. The ionic liquid 601 can vary in size and thickness. A typical application would see thickness from 10 μm to 10 mm, with a diameter of 100 μm to 5 mm.

In more detail, still referring to FIG. 2, the UV window 303 is well known to those skilled in the art of UV light sources. The UV window is selected to allow the preferred wavelengths of photons to pass from the UV bulb 301 into the sample chamber 400. As previously noted, in some embodiments, the UV light will be in the range of about 3 eV to about 12 eV and in other embodiments, the UV light may be in the range of about 8 eV to about 12 eV. As the UV light ionizes VOCs, the bias circuit 700 will generate a potential between the chamber walls 401 and the circuit board 650. It will be appreciated that when a volatile organic compound is ionized by UV light, one or more electrons are emitted, and if the chamber walls are at a positive potential to the circuit board, the electrons will be attracted to the chamber walls. Conversely, once a volatile organic compound has lost an electron, it will be attracted towards the circuit board at a lower potential than the chamber walls.

In more detail, still referring to FIG. 2, the circuit board 650 can be electrically connected to the ionic liquid 601, as ionic liquids are typically conductive. The circuit board 650 can also be electrically insulated from the ionic liquid 601.

Figure 3:
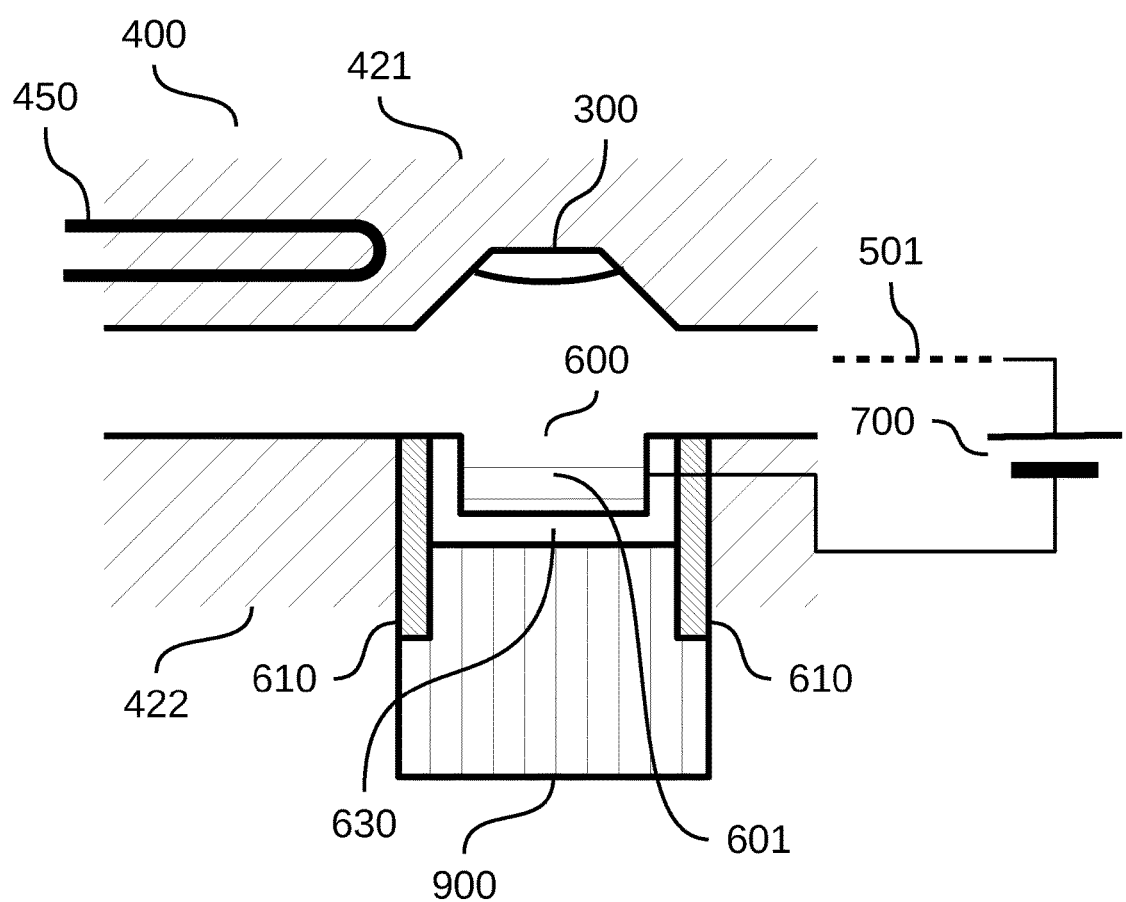
FIG. 3 is a partial longitudinal sectional view of another embodiment of the present invention, which depicts a gas sensing device with an ionization source (300), a sample chamber (400) and its parts, a counter electrode (501), and an ionic liquid trap (600) and its parts.

Referring now to FIG. 3, here is a partial longitudinal section of one embodiment of the present invention. In this embodiment the ionization source 300 is embedded in the sample chamber 400 and the sample chamber includes a ceiling 421, a floor 422, and an optional heating element 450. In one embodiment, the ionization source is selected from electromagnetic radiation, electron impact radiation (such as from an electron gun), radioactive material, and high speed particles. Under the ionization source 300 there is the ionic liquid trap 600. The ionic liquid trap is comprised of optional insulators 610, which separate the ionic liquid 601 from the chamber floor 422. The ionic liquid may be held in an optional container 630 and a temperature control unit 900 may be located under the optional container. In this embodiment, the bias circuit 700 uses a counter electrode 501. The bias circuit is also electrically connected to the ionic liquid 601.

In more detail, still referring to FIG. 3, an air sample enters the sample chamber 400 through a gas port (not shown) and travels between the chamber ceiling 421 and the chamber floor 422. As the air sample is exposed to the ionization source 300, VOCs become ionized. In one embodiment, the ionization source may be selected from any of the ionization sources described and defined herein. In another embodiment, the ionization source is selected from the group consisting of electromagnetic radiation, electron impact radiation (such as from an electron gun), radioactive material, high speed particles, and combinations thereof.

The electric field generated by the bias circuit 700 between the ionic liquid 601 and the counter electrode 501 will drive the ionized VOCs into the ionic liquid.

In more detail, still referring to FIG. 3, an optional heating element 450 may be connected or embedded into the sample chamber 400. This heating elemental can run between 30-500° C. The heating elemental can be used to prevent VOCs from condensing out of the air sample. The heating element can also be used to help clean the sample chamber.

In more detail, still referring to FIG. 3, an optional container 630 can used to hold the ionic liquid 601. In some embodiments, the optional chamber may be replaceable.

In more detail, still referring to the invention of FIG. 3, the volume of ionic liquid 601 in the sample chamber 400 may vary from 0.1 nanoliters to 100 milliliters.

In more detail, still referring to FIG. 3, the ionic liquid 601 can be electrically or thermally isolated from the floor 422 of the sample chamber 400 by insulators 610. The insulators can simultaneously isolate the ionic liquid electrically and thermally from the floor.

In more detail, still referring to FIG. 3, the ionic liquid 601 can be temperature controlled using a temperature control unit 920. The temperature range would be from −50-500° C.

In more detail, still referring to the invention of FIG. 3, the counter electrode 501 connected to the bias circuit 700 may be located outside of the sample chamber 400. The counter electrode may also be located inside the sample chamber.

In more detail, still referring to FIG. 3, the counter electrode 501 can be a conductive element in contact with the air sample, including but not limited to the floor 422 and ceiling 421 of the sample chamber 400.

Figure 4:
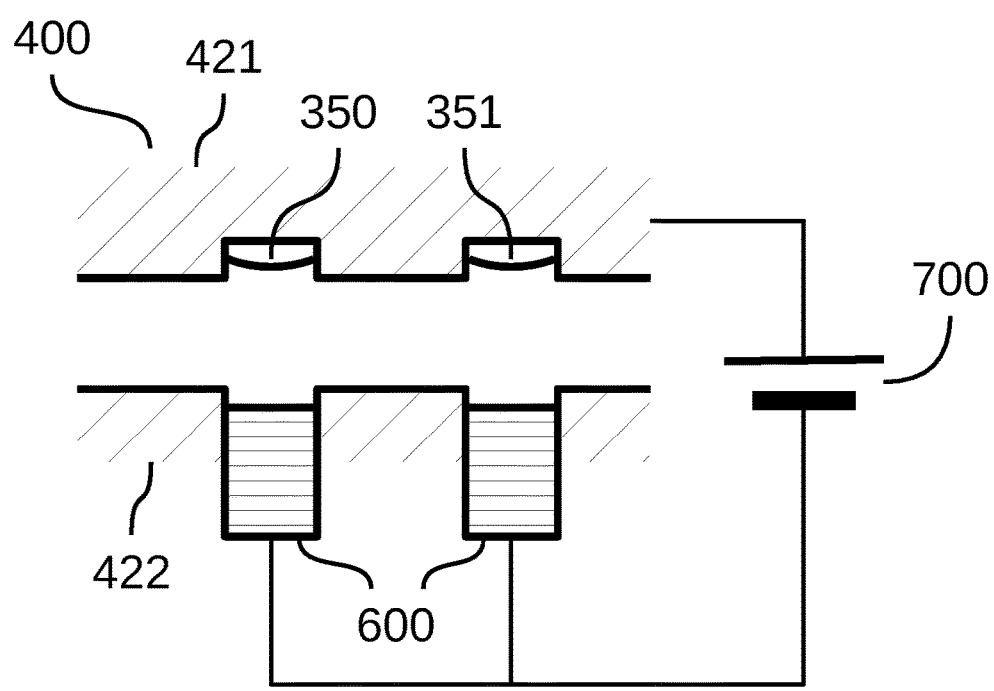
FIG. 4 is a partial longitudinal sectional view of a further embodiment of the present invention, which depicts a gas sensing device with two ionization sources (350, 351), a sample chamber (400) and its parts, two ionic liquid traps (600), and a bias circuit (700).

Referring now to FIG. 4, here is a partial longitudinal section of one embodiment of the present invention. The sample chamber 400 is made up of a floor 422 and ceiling 421. Inside the sample changes are multiple ionization sources 350, 351. In one embodiment, the ionization sources may be selected from any of the ionization sources described and defined herein. In another embodiment, the ionization sources are selected from the group consisting of electromagnetic radiation, electron impact radiation (such as from an electron gun), radioactive material, high speed particles, and combinations thereof. Under each ionization source there is an ionic liquid trap 600. The ionic liquid trap is connected to the bias circuit 700 which is connected to the chamber floor 422. In one embodiment, the device may include an optional temperature control unit or heating element under the ionic liquid trap (not shown).

In more detail, still referring to FIG. 4, an air sample enters the sample chamber 400 through a gas input port (not shown) and travels between the chamber ceiling 421 and the chamber floor 422. As the air sample is exposed to the ionization sources 350 and 351, VOCs become ionized. An electric field generated by the bias circuit 700 between the ionic liquid trap 600 and the chamber floor 422 drives the ionized VOCs into the ionic liquid in the ionic liquid trap. In one embodiment, the sample ceiling 421 acts as the counter electrode for the bias circuit.

With further reference to FIG. 4, in one embodiment, the ionization sources 350 and 351 may be the same type of ionization source or they may be different. For example, one ionization source may be UV light while the other ionization source may be a radioactive source. In another embodiment, the ionization sources 350 and 351 may have different ionization energies. By using different ionization energies, it is possible to separate different VOCs into different ionic liquid traps 600. It is to be understood that the two ionization sources (350, 351) shown in FIG. 4 are exemplary and that the gas sensing device of the present invention may have more than two ionization sources.

Figure 5:
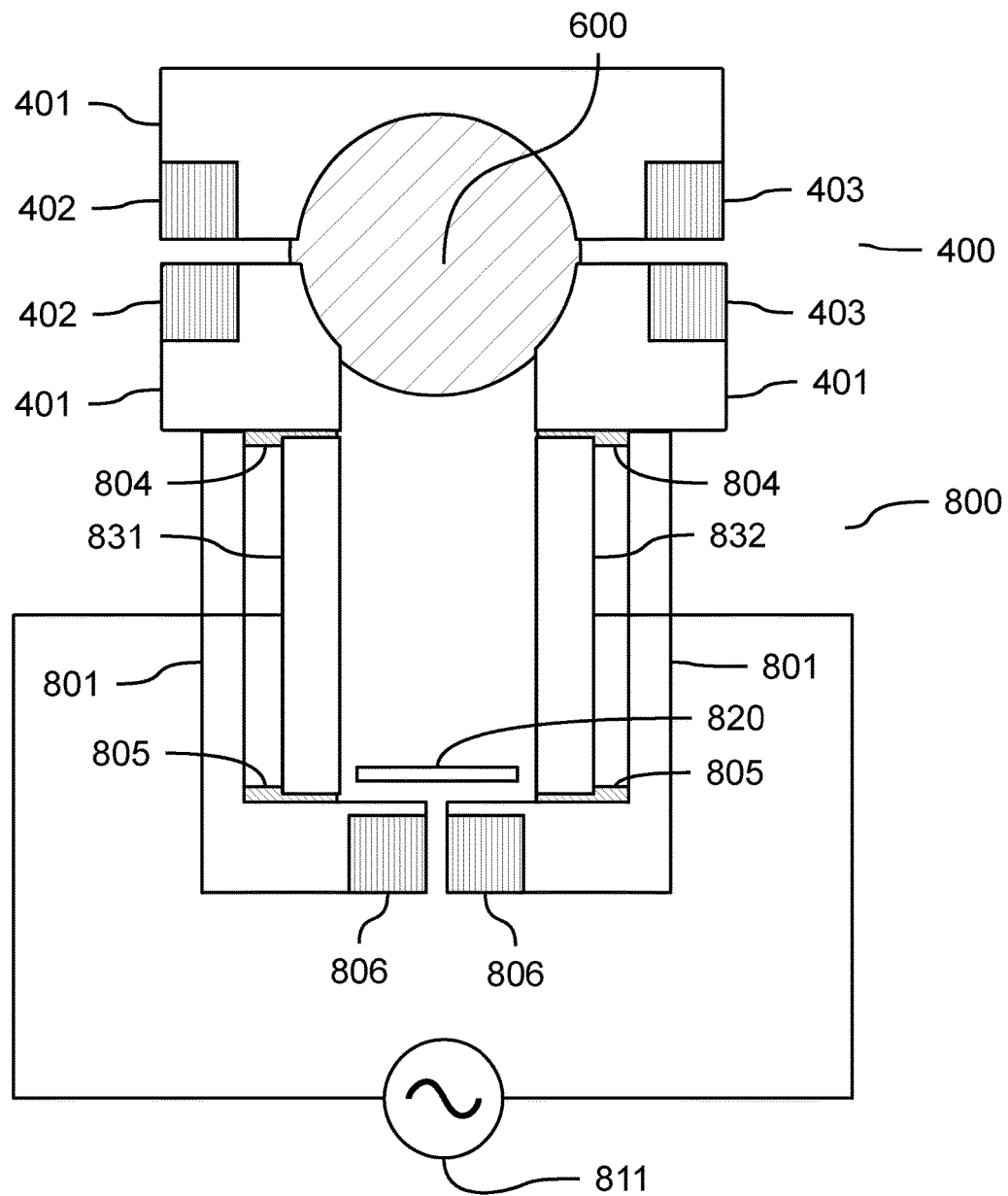
FIG. 5 is a partial cross sectional view of a further embodiment of the present invention, which depicts a gas sensing device with a sample chamber (400) and its parts, an ionic liquid trap (600), and a FAIMS (Field Asymmetric Ion Mobility Spectrometry)-enabled chemical sensor (800) and its parts.

Referring now to FIG. 5, here is a partial cross section of one embodiment of the present invention. In this embodiment a sample chamber 400, similar in configuration to the sample chamber of FIG. 2, is connected to an external chemical sensor 800. The sample chamber is comprised of the chamber walls 401. The sample chamber walls have a gas input port 402 and a gas output port 403. At the bottom of the sample chamber 400 is the ionic liquid trap 600 (the location of the ionic liquid trap at the bottom of the sample chamber is similar to that shown in FIG. 2). The chemical sensor 800 is composed of an exterior wall 801 that houses a pair of electrodes: the left plate 831 and the right plate 832. The chamber insulator 804 is placed between the left plate and the right plate and the chamber walls. Between the exterior wall and the left plate and the right plate is the sensor insulator 805. The chemical sensor 800 also has an outlet port 806 in the exterior walls. Between the left plate and the right plate is the ion sensor 820. The left plate and the right plate are connected to a RF source 811.

In more detail, still referring to FIG. 5, an air sample is admitted by the gas input port 402 into the sample chamber 400. After a period of time, the air sample is purged from the sample chamber by blowing neutral gas through the gas input port and allowing it to flow out of the gas output port 403. The gas output port 403 is then closed, and the chemical sensor outlet port 806 is opened. The neutral gas can now move through the chemical sensor 800. While the neutral gas is moving through the chemical sensor, an electric waveform from the RF source 811 is applied between the left plate 831 and the right plate 832.

In more detail, still referring to FIG. 5, once an air sample is admitted by the gas input port 402 into the sample chamber 400, the VOCs are captured into the ionic liquid trap 600. Once a sufficient number of VOCs have been collected into the ionic liquid trap, the neutral gas is used to clear out the air sample by blowing it in from the gas input port and expelling it through the gas output port 403. The gas output port 403 is then closed, and the VOCs are released from the ionic liquid trap, while the neutral gas now flows out of the opened chemical sensor outlet port 806. As VOCs are released from the ionic liquid trap they are ionized by using one or more techniques, known to those skilled in the art. Ionized VOCs in the neutral gas are subjected to an electrical waveform between the left plate 831 and the right plate 832 from the RF source 811. This electrical waveform determines which ionized VOCs hit the ion sensor 820 at the end of the chemical sensor 800. In more detail, still referring to FIG. 5, the size of the chemical sensor 800 can vary. It will be appreciated by those skilled in the art, that it may be as small as a few millimeters in length and width, but it can be made up to almost any size desired.

In more detail, still referring to FIG. 5, the same ionization source in the sample chamber 400 may be reused, or alternatively, another ionization source in the chemical sensor 800 may be used. In one embodiment, the ionization source(s) may be selected from any of the ionization sources described and defined herein. In another embodiment, the ionization source(s) may be selected from the group consisting of electromagnetic radiation, electron impact radiation (such as from an electron gun), radioactive material, high speed particles, and combinations thereof.

In more detail, still referring to FIG. 5, it will be appreciated by those skilled in the art, that the VOCs can be released from the ionic liquid trap 600 via any of the excitement methods previously mentioned herein.

In more detail, still referring to FIG. 5, it will be appreciated by those skilled in the art, that the VOCs released from the ionic liquid trap 600 may be ionized by any of the ionization sources previously described and defined herein. In one embodiment, the ionization source may be selected from the group consisting of electromagnetic radiation, electron impact radiation (such as from an electron gun), radioactive material, high speed particles, and combinations thereof.

In more detail, still referring to FIG. 5, the chemical sensor 800 shown therein is known as a Field Asymmetric Ion Mobility Spectrometry (FAIMS). As will be appreciated by those of skill in the art, within the context of the present invention, other ion mobility systems may be used instead of a FAIMS-based chemical sensor.

A further advantage of the present invention is, thus, the ability of the gas sensing system to separate VOCs to allow the IMS or FAIMS systems to measure their concentrations without interference from competing chemical species. For example, in a conventional IMS or FAIMS device, VOCs with high ionization energy are hard to detect in the presence of VOCs with low ionization energy. If the VOCs are released from the ionic liquid trap 600 by heat, high ionization energy VOCs tend to be released before low ionization energy VOCs, allowing good separation of the VOCs in the IMS or FAIMS.

Figure 6:
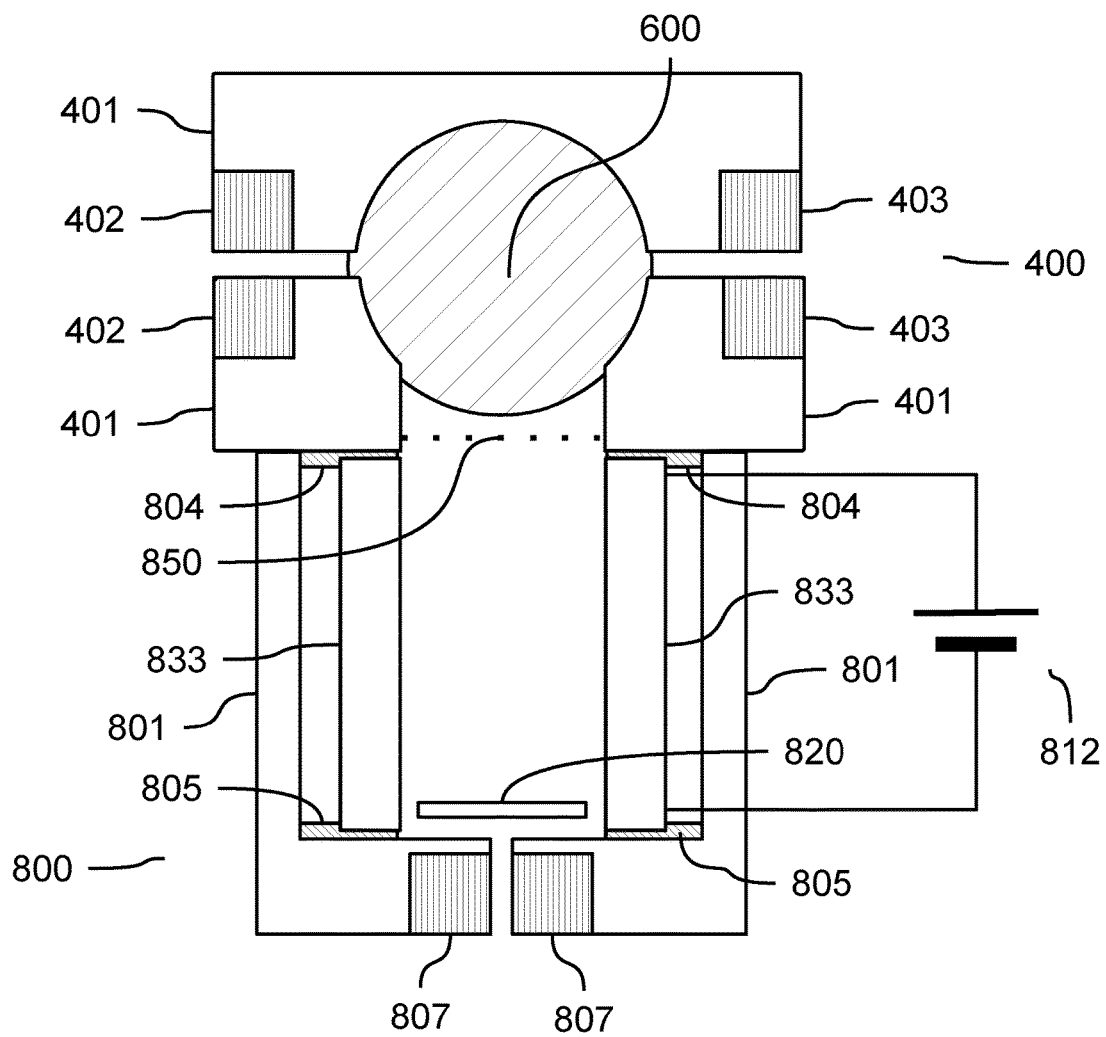
FIG. 6 is a partial cross sectional view of another embodiment of the present invention, which depicts a gas sensing device with a sample chamber (400) and its parts, an ionic liquid trap (600), and an IMS (Ion Mobility Spectrometry)-enabled chemical sensor (800) and its parts.

Referring now to FIG. 6, here is a partial cross section of another embodiment of the present invention. In this embodiment the sample chamber 400 is connected to an external chemical sensor 800. The sample chamber is comprised of the chamber walls 401. The sample chamber walls have a gas input port 402 and a gas output port 403. At the bottom of the chamber is shown the ionic liquid trap 600. The chemical sensor 800 is composed of an exterior wall 801 that houses one or more focusing electrodes 833. The focusing electrodes are connected to a focusing bias voltage 812. The chamber insulator 804 is placed between focusing electrodes and the chamber walls. Between the exterior wall and the focusing electrodes is the sensor insulator 805. The chemical sensor also has an inlet port 807 in the exterior wall. Near the focusing electrodes there is an ion gate 850, and at the other end of the focusing electrodes there is an ion sensor 820.

In more detail, still referring to FIG. 6 the ion sensor 820 may have a guard electrode placed in close proximity to the ion sensor, and located between the ion sensor and the ion gate 850. The guard electrode reduces capacitance interference from the charged VOCs heading towards the ion sensor.

In more detail, still referring to FIG. 6, an air sample is admitted by the gas input port 402 into the sample chamber 400. After a period of time, the air sample is purged from the sample chamber by blowing neutral gas through the gas input port and allowing it to flow out of the gas output port 403. The gas input port 403 is then closed, and the chemical sensor inlet port 807 is then opened. Neutral gas is then blown through the chemical sensor inlet port 807. VOCs released from the ionic liquid trap 600 must be ionized using one or more techniques, known to those skilled in the art. This ionization must occur prior to the VOCs reaching the ion gate 850. Periodically, the ion gate is opened. Ionized VOCs in the neutral gas are subjected to the electric field of the focusing electrodes 833. The electric field for the focusing electrodes is supplied by the focusing bias voltage 812.

In more detail, still referring to FIG. 6, once an air sample is admitted by the gas input port 402 into the sample chamber 400, the VOCs can be captured into the ionic liquid trap 600. Once a sufficient number of VOCs have been collected into the ionic liquid trap, the neutral gas is used to clear out the air sample by blowing it in from the gas input port and expelling it through the gas output port 403. The gas input port is then closed, and the VOCs are released from the ionic liquid trap, while the neutral gas now flows from the opened inlet port 807 through the gas output port 403. Ionized VOCs in the neutral gas are subjected to an electric field of the focusing electrodes 833. The ionized VOCs in the neutral gas are being moved by the focusing electrode in the opposite direction from the neutral gas. This separates them so that they arrive at the ion sensor 820 at different times.

In more detail, still referring to FIG. 6, the same ionization source in the sample chamber 400 may be reused, or alternatively, another ionization source in the chemical sensor 800 may be used. In one embodiment, the ionization source(s) may be selected from any of the ionization sources described and defined herein. In another embodiment, the ionization source(s) may be selected from the group consisting of electromagnetic radiation, electron impact radiation (such as from an electron gun), radioactive material, high speed particles, and combinations thereof.

In more detail, still referring to FIG. 6, it will be appreciated by those skilled in the art, that the VOCs can be released from the ionic liquid trap 600 via any of the excitement methods previously described and defined herein.

In more detail, still referring to FIG. 6, the chemical sensor 800 shown therein is known as an Ion Mobility Spectrometry (IMS). As will be appreciated by those of skill in the art, within the context of the present invention, other ion mobility systems may be used instead of an IMS-based chemical sensor.

Figure 7:
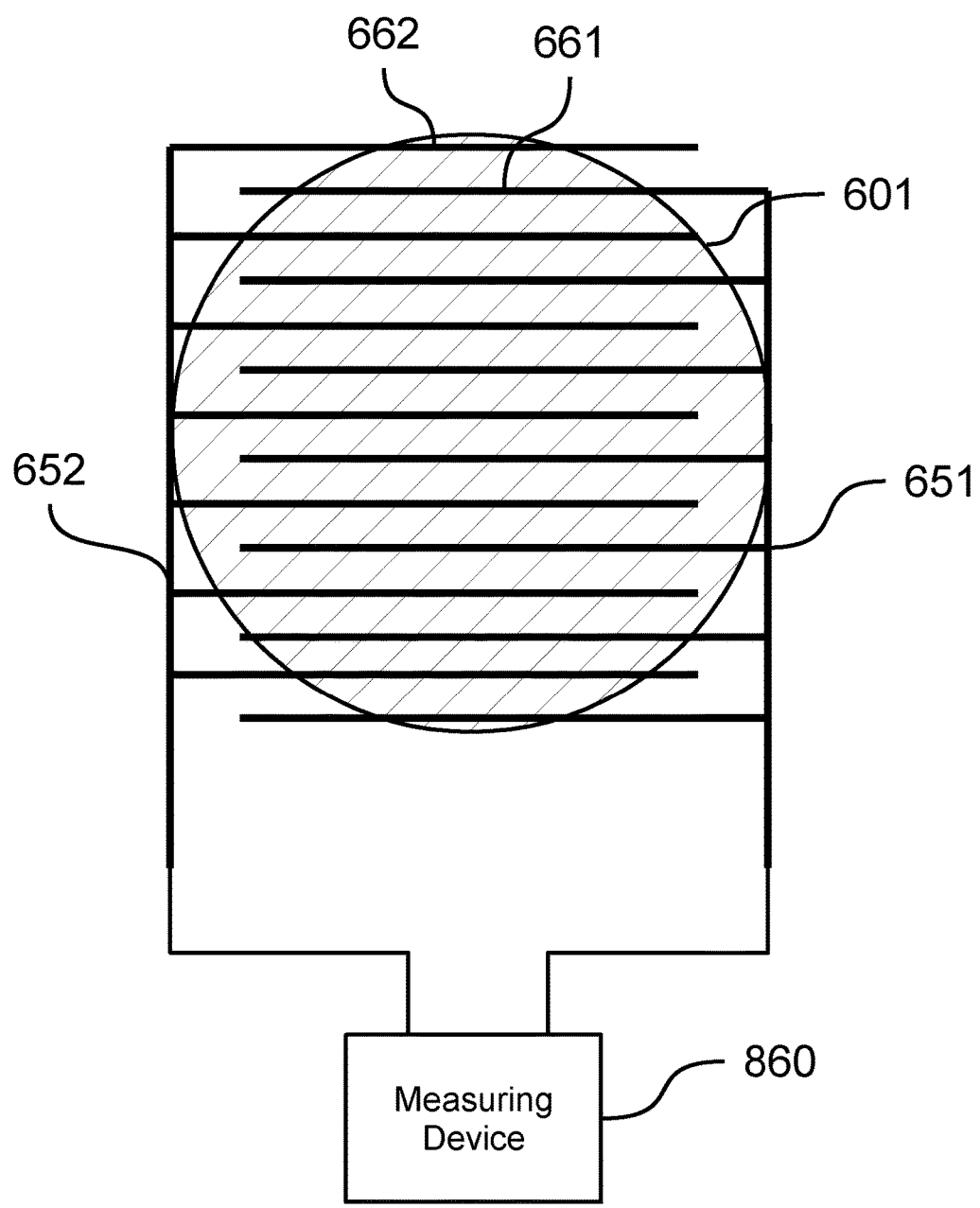
FIG. 7 is a partial top view of one embodiment of the gas sensing device of the present invention, which depicts heating elements for an ionic liquid trap and a measuring device for a chemical sensor.

Referring now to FIG. 7, here is a partial top view of one embodiment of the present invention. The ionic liquid 601 is placed on an insulating substrate that has left inter-digited electrodes 662 and right inter-digited electrodes 661 on the insulating substrate. The left inter-digited electrodes are connected to the left lead 652. The right inter-digited electrodes are connected to the right lead 651. The left lead and the right lead are connected to a measuring device 860, such as an Impedance Meter, that can measure the electrical properties of the circuit formed by the inter-digited electrodes 661 and 662 and the ionic liquid 601.

In more detail, still referring to FIG. 7, when VOCs are trapped in the ionic liquid 601 an electrical signal can be applied by the measuring device 860 to the left inter-digited electrodes 662 and right inter-digited electrodes 661. The voltage and/or current response to the electrical signal can then be read by the measuring device 860 to determine the complex impedance of the circuit formed by the inter-digited electrodes 661 and 662 and the ionic liquid 601. As will be clear to those skilled in the art, the measuring device 860 can be any number of devices developed for the purpose of measuring the electrical parameters of a circuit. Some examples of these devices are impedance meters, vector network analyzers, time-domain reflectometer, etc. As will also be clear to those skilled in the art, the analysis performed by the measuring device 860 on the circuit 661, 662, and 601 is also known as electrochemical impedance spectroscopy or dielectric spectroscopy.

In more detail, still referring to FIG. 7, the ionic liquid 601 will contain trapped VOCs. These trapped VOCs will alter the electrical properties of the circuit formed by the inter-digited electrodes 662 and 661 and the ionic liquid 601; and these changes can be measured by the measuring device 860.

In more detail, still referring to FIG. 7, the length of the left inter-digited electrodes 662 and the right inter-digited electrodes 661 can vary from under 1 micrometer to several centimeters. The widths of the left inter-digited electrodes and the right inter-digited electrodes can vary from under 1 micrometer to several centimeters. The number of the left inter-digited electrodes and the right inter-digited electrodes can vary from one a piece to several thousand.

Figure 8:
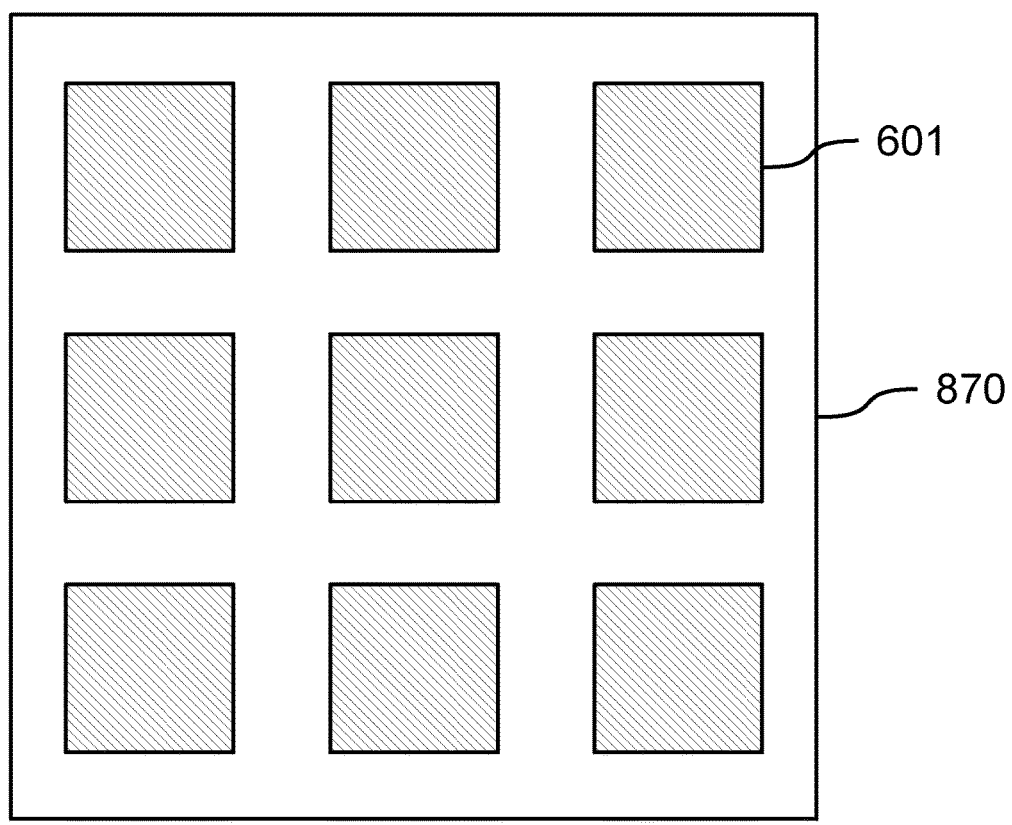
FIG. 8 is a partial top view of another embodiment of the gas sensing device of the present invention, which depicts an ionic liquid trap configured with an array of sensors containing ionic liquids.

Referring now to the invention in more detail, in FIG. 8, is a partial top view of one embodiment of the present invention. The sensor array 870 is comprised of a plurality of sensors containing ionic liquids 601.

In more detail, still referring to FIG. 8, the sensors containing ionic liquid 601 may be based on numerous technologies, including but not limited to, Ion Sensitive Field Effect Transistors (ISFET), dielectric spectroscopy, impedance, and viscosity changes.

In more detail, still referring to FIG. 8, the size of the sensor array 870 may range from sub-micrometer length and width, to several centimeters for length and width.

In more detail, still referring to FIG. 8, the number of sensors containing ionic liquid 601 on the sensor array 870 can vary from one to thousands.

In more detail, still referring to FIG. 8, the sensors containing ionic liquid 601 may contain different ionic liquids for each of the sensors.

In more detail, still referring to FIG. 8, the sensors containing ionic liquid 601 may have individual heating elements. Likewise, each of the sensors may have individual cooling systems. The heating and cooling elements may be shared across multiple elements in the sensor array 870.

The foregoing shows that an advantage of the present invention is that the gas sensing devices disclosed herein can measure any VOCs, even in the presence of competing chemical species.

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

We claim:
1. A device comprising:
a sample chamber for accepting a sample of air;
at least one ionization source for ionizing volatile organic compounds (VOCs);
an ionic liquid trap comprising an ionic liquid; and
a bias circuit for generating an electric field, wherein the bias circuit is connected to the ionic liquid trap and a conductive element of the device,
wherein ionization of VOCs in the sample of air by the ionization source and generation of the electric field by the bias circuit drives ionized VOCs from the sample chamber into the ionic liquid trap.

2. The device of claim 1, wherein the sample of air is measured in the range of about 10 mL to about 5000 L.

3. The device of claim 1, further comprising a chemical sensor for identifying the VOCs in the ionic liquid trap, wherein the chemical sensor is in communication with the ionic liquid trap.

4. The device of claim 3, wherein the chemical sensor further measures concentrations of the VOCs in the ionic liquid trap.

5. The device of claim 1, wherein the VOCs in the ionic liquid trap are released back into the sample chamber by excitation of the VOCs in the ionic liquid trap.

6. The device of claim 5, wherein the VOCs in the ionic liquid are excited by an energy source selected from the group consisting of heat, acoustic waves, ultrasound, microwaves, infrared radiation, pressure changes in the atmosphere above the iconic liquid trap, and combinations thereof.

7. The device of claim 5, further comprising a chemical sensor for identifying VOCs released from the ionic liquid trap to the sample chamber.

8. The device of claim 7, wherein the chemical sensor further measures concentrations of the VOCs released from the ionic liquid trap to the sample chamber.

9. The device of claim 1, wherein the sample chamber comprises an input port for accepting the sample of air.

10. The device of claim 9, wherein the sample chamber further comprises an output port.

11. The device of claim 10, wherein the input port and the output port are a single port.

12. The device of claim 10, wherein the sample chamber is cleaned by flushing a neutral gas through the input port and/or the output port.

13. The device of claim 12, wherein the neutral gas is clean air.

14. The device of claim 1, wherein the sample chamber comprises a floor, a ceiling, and an optional heating element.

15. The device of claim 14, wherein the heating element runs between about 30° C. to about 500° C.

16. The device of claim 14, wherein heating of the sample chamber prevents VOCs from condensing out of the air sample.

17. The device of claim 14, wherein the heating element is used to clean the sample chamber.

18. The device of claim 1, wherein the at least one ionization source is selected from the group consisting of electromagnetic radiation, ultraviolet (UV) light, radioactive material, corona discharge, chemical ionization, electron impact ionization, high speed particles,
x-ray ionization, electrospray, ion source, and combinations thereof.

19. The device of claim 18, wherein the at least one ionization source is electromagnetic radiation is in the range of about 1 µeV to about 16 eV.

20. The device of claim 18, wherein the at least one ionization source is UV light selected from the group consisting of direct current (DC) type UV bulbs with internal electrodes, lasers, excimer lamps, plasma, arc lamps, and light emitting diodes (LEDs).

21. The device of claim 18, wherein the at least one ionization source is UV light in the range of about 3 eV to 16 eV.

22. The device of claim 1, wherein the at least one ionization source comprises at least two different ionization sources to drive VOCs of differing ionization energies from the sample chamber to the different ionic liquid traps.

23. The device of claim 1, further comprising an electrical insulator to separate ionic liquids in the ionic liquid trap from the sample chamber.

24. The device of claim 1, further comprising a counter electrode for the bias circuit.

25. The device of claim 24, wherein the counter electrode is located in the sample chamber.

26. The device of claim 24, wherein the electric field is generated between the ionic liquid and the counter electrode.

27. The device of claim 1, wherein the ionization source is embedded in the sample chamber.

28. The device of claim 1, further comprising a moisture filter to reduce moisture content of the sample of air entering into the sample chamber.

29. The device of claim 1, wherein the sample of air is obtained from an animal.

30. The device of claim 29, wherein the animal is a human.

31. The device of claim 1, wherein the device is a hand-held or portable device.

32. A device comprising:
a sample chamber for accepting a sample of air;
at least one ionization source for ionizing volatile organic compounds (VOCs) present in the sample of air;
an ionic liquid trap comprising an ionic liquid that captures ionized VOCs from the sample chamber, wherein the ionized VOCs are deionized in the ionic liquid trap and reionized upon release from the ionic liquid trap; and
a chemical sensor in communication with the ionic liquid trap, wherein the chemical sensor identifies ionized VOCs released from the ionic liquid trap.

33. The device of claim 32, wherein the sample chamber comprises an input port for accepting the sample of air.

34. The device of claim 33, wherein the sample chamber further comprises an output port.

35. The device of claim 34, wherein the input port and the output port are a single port.

36. The device of claim 34, wherein the sample chamber is cleaned by flushing a neutral gas through the input port and/or the output port.

37. The device of claim 32, wherein the at least one ionization source is selected from the group consisting of electromagnetic radiation, ultraviolet (UV) light, radioactive material, corona discharge, chemical ionization, electron impact ionization, high speed particles,
x-ray ionization, electrospray, ion source, and combinations thereof.

38. The device of claim 37, wherein the at least one ionization source is electromagnetic radiation in the range of 1 µeV to 16 eV.

39. The device of claim 32, wherein the deionized VOCs in the ionic liquid trap are released back into the sample chamber by excitation of the VOCs in the ionic liquid trap.

40. The device of claim 39, wherein the VOCs in the ionic liquid are excited by an energy source selected from the group consisting of heat, acoustic waves, ultrasound, microwaves, infrared radiation, pressure changes in the atmosphere above the iconic liquid trap, and combinations thereof.

41. The device of claim 32, wherein the chemical sensor further measures concentrations of the ionized VOCs released from the ionic liquid trap to the sample chamber.

42. The device of claim 32, wherein the chemical sensor comprises an outlet port, an electrical waveform, and an ion sensor, wherein the ionized VOCs released from the ionic liquid trap pass through the outlet port and the electrical waveform directs the ionized VOCs to the ion sensor for identification.

43. The device of claim 32, wherein the chemical sensor comprises an inlet port and an ion sensor, wherein introduction of a neutral gas in a steady stream into the inlet port causes different ionized VOCs in the sample chamber to reach the ion sensor at different times.

44. The device of claim 43, wherein the neutral gas is clean air.

45. The device of claim 32, wherein the device is a hand-held or portable device.

46. A device comprising:

a sample chamber for accepting a sample of air;

at least one ionization source for ionizing volatile organic compounds (VOCs);

an ionic liquid trap comprising an ionic liquid; and a bias circuit for generating an electric field, wherein the bias circuit is connected to the ionic liquid trap and a conductive element of the device;

a chemical sensor for identifying and measuring concentrations of VOCs, wherein ionization of VOCs in the sample of air by the ionization source and generation of the electric field by the bias circuit drives ionized VOCs from the sample chamber into the ionic liquid trap.

47. The device of claim 46, wherein the ionic liquid trap further comprises a circuit and the chemical sensor comprises a measuring device selected from the group consisting of impedance meters, vector network analyzers, time-domain reflectometers, and combinations of thereof.

48. The device of claim 47, wherein upon application of an electric current from the measuring device to the circuit, altered electrical properties in the circuit are measured by the measuring device, wherein the electrical properties of the circuit are altered by VOCs in the ionic liquid trap.

49. The device of claim 46, wherein the ionic liquid trap comprises an array of sensors containing the ionic liquid, wherein each sensor in the array may contain the same ionic liquid or a different ionic liquid.

50. The device of claim 49, wherein the sensors are selected from the group consisting of ion sensitive field effect transistors (ISFET), dielectric spectroscopy, impedance, and viscosity changes, and combinations thereof.

51. The device of claim 49, wherein the sensors may have individual heating and/or cooling elements.

\* \* \* \* \*